United States Patent [19]

Moser

[11] 4,008,066
[45] Feb. 15, 1977

[54] PHENYLAMINOACETAMIDES FOR REGULATING PLANT GROWTH
[75] Inventor: Hans Moser, Magden, Switzerland
[73] Assignee: Ciba-Geigy Corporation, Ardsley, N.Y.
[22] Filed: Oct. 15, 1975
[21] Appl. No.: 622,595

Related U.S. Application Data
[63] Continuation-in-part of Ser. No. 458,970, April 8, 1974, abandoned.

[52] U.S. Cl. .................................. 71/76; 71/118; 260/558 A; 260/559 A; 260/562 B
[51] Int. Cl.² ............... A01N 9/20; C07C 103/22; C07C 103/78
[58] Field of Search ....... 260/562 B, 558 A, 559 A; 71/118, 76

[56] References Cited
UNITED STATES PATENTS

| 2,676,188 | 4/1954 | Bruce et al. | 260/562 B X |
| 3,345,151 | 10/1967 | Olin | 71/76 X |
| 3,547,620 | 12/1970 | Olin | 71/118 |
| 3,637,847 | 1/1972 | Olin | 71/118 X |
| 3,712,805 | 1/1973 | Yates et al. | 260/562 B X |
| 3,769,301 | 10/1973 | Olin | 260/326.45 |
| 3,780,090 | 12/1973 | Akiba et al. | 71/115 X |
| 3,829,306 | 8/1974 | Ratts | 71/118 X |
| 3,830,841 | 8/1974 | Ratts | 260/558 P X |
| 3,853,531 | 12/1974 | Ratts | 71/76 |
| 3,901,685 | 8/1975 | Ratts | 71/118 |
| 3,907,544 | 9/1975 | Olin | 71/118 X |
| 3,944,607 | 3/1976 | Chan | 71/118 X |
| 3,952,056 | 4/1976 | Vogel et al. | 71/118 X |
| 3,966,811 | 6/1976 | Krenzer | 71/118 X |

OTHER PUBLICATIONS
Clayton et al., CA 80:59719w (1974).
B413,379, Mar. 1976, Bluestone et al., 71/118 X.

Primary Examiner—Daniel E. Wyman
Assistant Examiner—Thomas A. Waltz
Attorney, Agent, or Firm—Harry Falber

[57] ABSTRACT
Compounds of the general formula

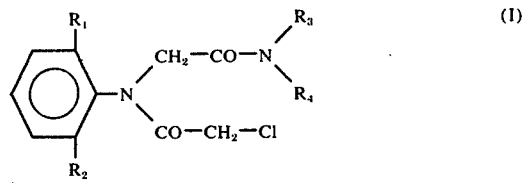

wherein $R_1$ and $R_2$ each represents methyl or ethyl, or wherein $R_1$ represents chlorine or methoxy and $R_2$ represents methyl, and $R_3$ and $R_4$ each represents hydrogen, methyl or ethyl.

20 Claims, No Drawings

PHENYLAMINOACETAMIDES FOR REGULATING PLANT GROWTH

CROSS REFERENCE

This application is a continuation-in-part of our application Ser. No. 458,970, filed Apr. 8, 1974 now abandoned.

The present invention provides phenylaminoacetamides, plant regulating agents which contain these new compounds as active ingredients, and a method for regulating plant growth, in particular for delaying the growth of grasses and crop plants and for combatting weeds, which comprises the use of the new active substances or of the agents which contain them.

The new compounds have the formula

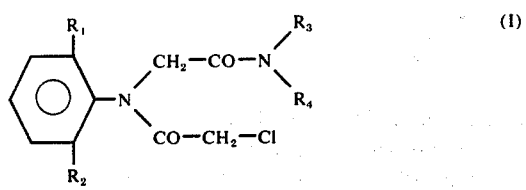

wherein $R_1$ and $R_2$ each represents methyl or ethyl, or wherein $R_1$ represents chlorine or methoxy and $R_2$ represents methyl, and $R_3$ and $R_4$ each represents hydrogen, methyl or ethyl.

A preferred group of compounds according to formula I are those wherein $R_1$ and $R_2$ each represents methyl or ethyl, or wherein $R_1$ represents chlorine and $R_2$ represents methyl, $R_3$ and $R_4$ each represents hydrogen, methyl or ethyl, the total number of carbon atoms in $R_1$ to $R_4$ not exceeding six.

U.S. Pat. No. 3,780,090 teaches the use of 2,6-dialkylphenylaminoacetic acid esters as herbicides. However, the action even of those representatives singled out as being preferred, e.g. N-(2,6-diethylphenyl)-N-chloroacetyl-aminoacetic acid ethyl ester, is unsatisfactory in many respects (plant selectivity, duration of action, rate of application). Mention is not made of plant regulating properties other than herbicidal effects.

A number of these representatives, including N-(2,6-diethylphenyl)-N-chloroacetyl-aminoacetic acid ethyl ester, are also comprehended and cited in German Offenlegungsschrift 2,311,897 of earlier priority (U.S. application Ser. Nos. 233,817 and 233,818). But besides these compounds there are also specified a larger number of N-substituted phenylamines with immensely widely varying structures which not only do not attain the herbicidal action of the type of compound cited hereinabove but are partly totally inactive or even destroy crop plants and leave the weeds unaffected. To the expert the teaching of German Offenlegungsschrift 2.311.897 is that, within the very large group of N-(substituted)phenyl-N-haloacetyl-alkanecarboxylic acids or derivatives thereof, only the group of N-haloacetylated N-phenylacetic acid esters also cited in U.S. Pat. No. 3,780,090 is suitable for practical purpose for use as selective herbicides.

The present invention is based on the completely surprising observation that the very small group of N-phenylaminoacetamides of the formula I exhibits superior growth regulating effects.

The active substances according to the invention of the formula I are stable compounds and, applied before emergence of weeds possess very good herbicidal properties against annual grasses such as Panicum and related plants of the genera Setaria, Digitaria etc., against grasses such as Lolium Species and against many dicotyledonous weeds such as Amaranthus, Sesbania, Chrysanthemum, Ipomoea, Galium, Sinapis, Pastinaca etc., without causing damage to the crop plants for which the use of the active substances is intended, for example soya, alfalfa, peas, lentils, ground nuts, cotton, maize, coffee, tea, bananas, pineapples, sugar beet, sugar cane, potatoes, paprika, tomatoes, spinach, onions, aubergines, sun flowers, tobacco, Brassica species e.g. rape and cabbage, and also cereals such as barley, oats, rye, wheat, dry rice or water rice, as well as the cultivated grain sorghum.

It is to be observed in this connection that, within the active substance group of the formula I, individual compounds possess varying selectivity in the cultures of crops plants. However, all the compounds of the formula I have in common the selective control of grasses, chiefly of annual grasses (Panicum varieties) in cultures of crop plants, in very low rates of application.

Of the compounds of the formula I particular interest attaches to the subgroup in which $R_1$ represents chlorine or methoxy, $R_2$ represents methyl, $R_3$ represents hydrogen, methyl or ethyl, and $R_4$ represents methyl or ethyl.

A further preferred subgroup of the formula I is that wherein $R_1$ and $R_2$ each represents methyl or ethyl, $R_3$ represents hydrogen, methyl or ethyl, and $R_4$ represents methyl or ethyl.

Examples of preferred compounds for controlling weeds in cotton and/or surgar beet and/or soya and for retarding the growth in height of grasses and crop plants such as soya are:
N-methyl-[N'-(2,6-dimethylphenyl)-N'-chloroacetylamino]-acetamide; N-methyl-[N'-(2-methyl-6-ethylphenyl)-N'-chloroacetyl-amino]-acetamide; N,N-dimethyl-[N'-(2,6-dimethylphenyl)-N'-chloroacetylamino]-acetamide; N,N-dimethyl-[N'-(2-methyl-6-ethylphenyl)-N'-chloroacetylamino]-acetamide; N-ethyl-[N'-(2,6-dimethylphenyl)-N'-chloroacetylamino]-acetamide; N-ethyl-N'-(2-methyl-6-ethylphenyl)-N'-chloroacetylamino]-acetamide; N,N-dimethyl-[N'-(2-chloro-6-methylphenyl)-N'-chloroacetyl-amino]-acetamide; N-methyl-[N'-(2-chloro-6-methylphenyl)-N'-chloroacetylamino]-acetamide; N-methyl[N'-(2,6-diethylphenyl)-N'-chloroacetylamino]-acetamide.

Naturally still other cultures are suitable besides the three large-scale ones mentioned hereinabove.

Furthermore, the active substances of the formula I increase the tillering of crop plants. Profusely and rapidly seeding weeds are inhibited in their germination and emergence and consequently removed from the cultures of crop plants. Sucker control is achieved with the active substances chiefly in tobacco.

In many types of plants, such as soybeans, potatoes, sugar cane, beets, grape-vines, fruit trees and tobacco, the retardation of vegetative growth or axillary shoots caused by compounds of formula I results in increase of fruit or other yield of the plants at harvest. It is further believed that by suppressing such growth at the appropriate stage of development less of the available carbohydrate is consumed as plant nutrition with a consequent enhancement of the starch or sucrose content.

As a result the storage capacity of substances contained in plants is as a rule improved by the active substances according to the invention. For example, the sugar content in sugar beet and sugar cane or the starch content in potatoes or the fat content in soya beans or ground nuts is increased by a number of representatives of the formula I.

The compounds of the formula I also possess in part defoliating properties and can be applied to delay blossoming.

The herbicidal application of the active substances is effected before the germination of the crops plants and weeds. The rates of application are between 0.1 and 10 kg of active substance per hectare. But the weeds are almost completely destroyed at a rate of application as low as 0.25 kg of active substance per hectare. Normally up to 10 kg of active substance per hectare are used to prevent railway embankments, factory grounds, roads etc. from becoming overgrown with weeds.

The plant growth regulating properties come to light preferably at postemergent application or later. The rates of application are between 0.25 kg and 10 kg of active substance per hectare depending on the type of the plants, their stage of development, the climate and other factors.

The new compounds of the formula I are manufactured by reacting a phenylaminoacetamide of the formula II

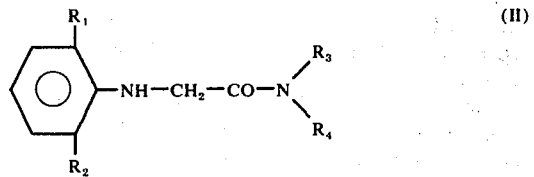
(II)

with a chloroacylating agent, preferably an anhydride or halide or chloroacetic acid. In the formula II, $R_1$, $R_2$, $R_3$ and $R_4$ have the same meanings as given under the formula I.

The starting materials of the formula II are manufactured by conventional methods, advantageously by one of the following three methods:

a. the corresponding aniline of the formula III

(III)

is reacted with a haloacetamide of the formula IV

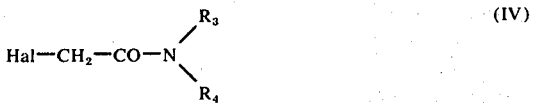
(IV)

in the presence of a weak to medium strength inorganic base;

b. the corresponding aniline of the formula III is reacted with a haloacetic acid ester of the formula V

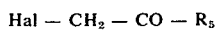
V.

in the presence of a weak to medium strength base to give the intermediate of the formula VI

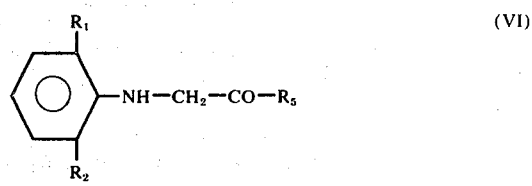
(VI)

and the resulting ester is then converted with surplus amine of the formula VII

(VII)

to the acid amide of the formula II;

c. the corresponding aniline of the formula III is reacted according to the method described in "Org. Chem., Vol. 22, 1099 [1957] with a solution of formaldehyde/$NaHSO_3$ and the resulting sodium salt of N-phenylaminomethanesulphonic acid of the formula VIII

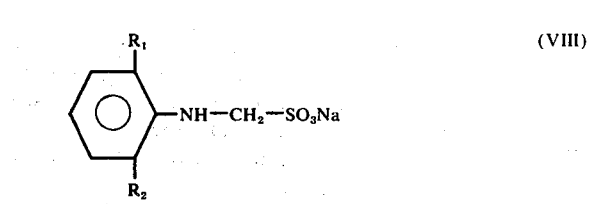
(VIII)

is reacted with potassium cyanide to give the nitrile of the formula IX

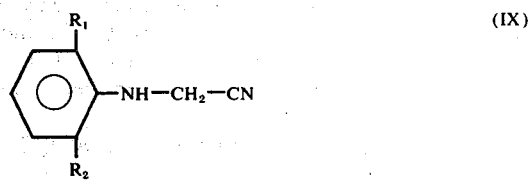
(IX)

which, by heating with e.g. sodium hydroxide solution, yields either the free 2,6-disubstituted N-phenylaminoacetic acid from which the desired intermediate of the formula II is obtained by reaction with the corresponding amine VII, or, if $R_3 = R_4 =$ hydrogen, the unsubstituted amide of the formula II is obtained by partial saponification of the nitrile IX.

In the formulae III to IX, the symbols $R_1$, $R_2$, $R_3$ and $R_4$ have the meanings given for the formula I, "Hal" represents chlorine or bromine, and $R_5$ represents the phenolic or alcohol radical in the ester, preferably a lower alkoxy radical such as methoxy or ethoxy.

The reactions can be carried out in the presence of or without solvents or diluents which are inert towards the reactants. Examples of suitable solvents or diluents are: aliphatic, aromatic or halogenated hydrocarbons, e.g. benzene, toluene, xylene, petroleum ether, chlorobenzene, methylene chloride, ethylene chloride, chloroform; ethers and ethereal compounds, e.g. dialkyl ether, dioxan, tetrahydrofuran; nitriles, e.g. acetonitrile, and mixtures of these solvents.

As suitable chloroacetylating agents there are preferably used chloroacetic anhydride and chloroacetic halides, e.g. chloroacetyl chloride or chloroacetyl bromide. But it is also possible to carry out the reaction with the esters or amides thereof. The reaction temperatures are between 0° C and 200° C, preferably between 20° C and 100° C. Often, especially if chloroacetyl halides are used, the chloroacetylation is carried out in the presence of an acid acceptor. Suitable acid acceptors are: tertiary amines, such as trialkylamines, e.g. triethylamine, pyridine and pyridine bases or inorganic bases such as oxides and hydroxides, hydrogen carbonates and carbonates of alkali metals and alkaline earth metals. Furthermore, it is also possible to use the respective aniline of the formula II as acid acceptor, in which case a surplus thereof must be used. Suitable weak to medium strength bases in the manufacture of the intermediates of the formula II are preferably alkali carbonates or hydrogen carbonates.

The following Examples illustrate the process of manufacturing. The active substances obtained according to the Examples and further active substances of the formula I which were manufactured by one of the above mentioned processes are listed in the subsequent Table.

EXAMPLE 1

A. Manufacture of the intermediate 83 g of bromoacetic acid methyl amide and 169 ml of 2,6-dimethyl aniline are stirred for 10 hours at 140° C bath temperature. The reaction mixture is left to stand overnight at room temperature. Next morning the contents of the flask are crystallised right through. The contents are filtered off and the precipitate is washed with benzene. The precipitate is subsequently dissolved in a small amount of water, the solution is brought to a pH of 10 to 11 with 30% sodium hydroxide solution and extracted with ether. The ethereal extract is dried over sodium sulphate, the ether distilled off in vacuo, and the residue is distilled in a high vacuum to yield 55 g of 2,6-dimethylanilinoacetic acid methyl amide (b.p. 152°–154° C/0.1 Torr). After recrystallisation from diisopropyl ether the product melts at 71°–73° C. 2,6-dimethylanilinoacetic acid dimethyl amide was manufactured in analogous manner: b.p. 132° C/0.3 Torr; m.p. 52°–54° C (recyrstallisation from diisopropyl ether/petroleum ether).

B. Manufacture of Compound No. 2

31.4 g of 2,6-dimethylanilinoacetic acid methyl amide are dissolved in 250 ml of chlorobenzene. 1.5 ml of dimethyl formamide are added to this solution and the mixture is heated to 110° C. At this temperature 14.3 ml of chloroacetyl chloride are added dropwise with stirring. After 1 ½ hours the evolution of HCl has virtually ceased. The reaction mixture is allowed to cool and concentrated in a rotary evaporator to leave as residue a blackish-brown oil which is crystallised from ethyl acetate with the addition of animal charcoal. Yield: 22.4 g of N-methyl-[N'-(2,6-dimethylphenyl)-N'-chloroacetylamino]-acetamide (m.p. 140° C-142° C). N,N-dimethyl-(N'-(2,6-dimethylphenyl)-N'-chloroacetylamino]-acetamide was obtained in analogous manner; m.p. 74°–76° C (from ether).

EXAMPLE 2

A. Manufacture of the intermediate 22.3 g of 2,6-dimethylanilinoacetic acid methyl ester are dissolved in 150 ml of absolute methanol and dry ammonia is passed in with stirring until the solution is saturated. In the course thereof the temperature rises to 37° C. The reaction mixture is left to stand overnight. It is then concentrated in vacuo to leave as residue a yellow oil which crystallises on scratching. Recrystallisation from toluene yields 15.3 g of 2,6-dimethylanilino acetic acid amide which melts at 89°–92° C.

B. Manufacture of Compound No. 1

12.4 g of potassium carbonate and 0.5 ml of water are added to a solution of 14,5 g of 2,6-dimethylanilinoacetic acid amide in 150 ml of methyl ethyl ketone and 7.15 ml of chloroacetyl chloride are added dropwise thereto with stirring. The temperature rises in the process to 39° C and $CO_2$ is evolved. The reaction mixture is stirred for 3 hours at room temperature, filtered and concentrated in vacuo to dryness. The crystalline residue is recrystallised from ethyl acetate to yield 6.3 g of N-chloroacetyl-N-(2,6-dimethylphenyl)-amino-acetamide (m.p. 135°–137° C).

In this manner or analogously the compounds listed in the Table can be obtained.

Table $$\text{(I)} \quad \text{Ar}(R_1)(R_2)\text{-N}(CH_2\text{-CO-N}(R_3)(R_4))(CO\text{-CH}_2Cl)$$

| Comp. No. | $R_1$ | $R_2$ | $R_3$ | $R_4$ | Physical Constants |
|---|---|---|---|---|---|
| 1 | $CH_3$ | $CH_3$ | H | H | mp.135–137° |
| 2 | $CH_3$ | $CH_3$ | H | $CH_3$ | mp.140–142° |
| 3 | $CH_3$ | $CH_3$ | $CH_3$ | $CH_3$ | mp.74–76° |
| 4 | $CH_3$ | $CH_3$ | H | $C_2H_5$ | mp.142–145° |
| 5 | $CH_3$ | $CH_3$ | $CH_3$ | $C_2H_5$ | mp.74–78° |
| 6 | $CH_3$ | $CH_3$ | $C_2H_5$ | $C_2H_5$ | bp.168°/0.001 Torr. |
| 7 | $CH_3$ | $C_2H_5$ | H | H | mp.109–112° |
| 8 | $CH_3$ | $C_2H_5$ | H | $CH_3$ | mp.109–111° |
| 9 | $CH_3$ | $C_2H_5$ | $CH_3$ | $CH_3$ | mp.76–78° |
| 10 | $CH_3$ | $C_2H_5$ | H | $C_2H_5$ | mp.93–95° |
| 11 | $CH_3$ | $C_2H_5$ | $CH_3$ | $C_2H_5$ | $n_D^{22}$ 1.5390 |
| 12 | $CH_3$ | $C_2H_5$ | $C_2H_5$ | $C_2H_5$ | bp. 173°/0.001 Torr. |
| 13 | $C_2H_5$ | $C_2H_5$ | H | H | mp.146–148° |
| 14 | $C_2H_5$ | $C_2H_5$ | H | $CH_3$ | mp.133–135° |
| 15 | $C_2H_5$ | $C_2H_5$ | $CH_3$ | $CH_3$ | mp.80–82° |
| 16 | $C_2H_5$ | $C_2H_5$ | H | $C_2H_5$ | mp.139–142° |
| 17 | $C_2H_5$ | $C_2H_5$ | $CH_3$ | $C_2H_5$ | Oil |
| 18 | $C_2H_5$ | $C_2H_5$ | $C_2H_5$ | $C_2H_5$ | Oil |
| 19 | Cl | $CH_3$ | H | $CH_3$ | mp.112–114° |
| 20 | Cl | $CH_3$ | $CH_3$ | $CH_3$ | mp.84–86° |
| 21 | $CH_3O$ | $CH_3$ | H | $CH_3$ | mp.102–104° |
| 22 | $CH_3O$ | $CH_3$ | $CH_3$ | $CH_3$ | mp.117–119° |
| 23 | $CH_3O$ | $CH_3$ | H | H | mp.164–166° |
| 24 | Cl | $CH_3$ | H | H | mp.135–137° |

The agents according to the invention are manufactured in known manner by intimately mixing and grinding active substances of the general formula I with suitable carriers and/or dispersants, optionally accompanied by the addition of antifoaming agents, wetting agents, dispersants and/or solvents which are inert towards the active substances.

The active substances can take and be used in the following forms:

solid forms: dusts, tracking agents, granules, coated granules, impregnated granules and homogeneous granules;

active substance concentrates which are dispersable in water: wettable powders, pastes, emulsions;

liquid forms: solutions.

In the agents according to the invention, the active substances concentrations are from 1 to 80 percent by weight and can optionally also be in low concentrations, e.g. about 0.05 to 1%, for the application.

It is possible to admix other biocidal active substances or agents with the agents according to the invention described herein. Besides the cited compounds of the general formula I, the new agents can therefore contain e.g. insecticides, fungicides, bactericides, fungistatic agents, bacteriostatic agents, nematocides or further herbicides in order to broaden the activity spectrum.

Granules

The following substances are used to manufacture 5% granules:
  5 parts of one of the active substances of the formula I
  0.25 parts of epichlorohydrin,
  0.25 parts of cetyl polyglycol ether,
  3.50 parts of polyethylene glycol ether,
  91 parts of kaolin (particle size: 0.3–0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable powder

The following constituents are used to manufacture (a) a 70%, and (b) a 10% wettable powder:
a.
  70 parts of one of the active substances of the formula I,
  5 parts of sodium dibutylnaphthalene sulphonate,
  3 parts of naphthalenesulphonic acid/phenolsulphonic acid/formaldehyde condensate (3:2:1),
  10 parts of kaolin,
  12 parts of Champagne chalk;
b.
  10 parts of N-ethyl-[N'-(2,6-dimethylphenyl)-N'-chloroacetylamino]-acetamide,
  3 parts of a mixture of the sodium salts of saturated fatty alcohol sulphates,
  5 parts of naphthalenesulphonic acid/formaldehyde condensate,
  82 parts of kaolin.

The indicated active substance is applied to the corresponding carriers (kaolin and chalk and then these are mixed and ground to yield wettable powders of excellent wettability and having an excellent capacity for forming suspensions. By diluting these wettable powders with water it is possible to obtain suspensions with 0.1% to 8% of active substance which are suitable for retarding growth of cereals, grasses (lawn) and soya cultures.

Paste

The following substances are used to manufacture a 45% paste:
  45 parts of N-ethyl-[N'-(2-methyl-6-ethylphenyl)-N'-chloroacetylamino]-acetamide or one of the other cited active substances of the formula I,
  5 parts of sodium aluminium silicate,
  14 parts of cetyl polyglycol ether with 8 mols of ethylene oxide,
  1 part of oleyl polyglycol ether with 5 mols of ethylene oxide,
  2 parts of spindle oil,
  10 parts of polyethylene glycol,
  23 parts of water.

The active substance is intimately mixed with the addition in appropriate devices and ground. A paste is obtained from which, by diluting it with water, is possible to manufacture suspension of every desired concentration of active substance.

Emulsion Concentrate

To manufacture a 25% emulsion concentrate
  25 parts of N,N-dimethyl-[N'-(2-ethyl-6-methylphenyl)-N'-chloroacetylamino]-acetamide or one of the other cited active substances of the formula I,
  5 parts of a mixture of nonylphenolpolyoxy-ethoxyethylene and calcium, dodecylenesulphonate,
  35 parts of 3,5,5-trimethyl-2-cyclohexan-1-one,
  35 parts of dimethyl formamide,
are mixed together. This concentrate can be diluted with water to give emulsions in desired concentrations of e.g. 0.1% to 10%. Such emulsions are suitable for controlling weeds before germination and for delaying growth of grasses and soya plants.

EXAMPLE 3

Growth inhibition in grasses (postemergence method)

Seeds of the grasses Lolium perenne, Poa pratensis, Festuca ovina, and Dactylis glomerata were sown in plastic dishes filled with an earth/turf/sand mixture. After 3 weeks the germination grasses were cut back to a height of 4 cm above the soil and 2 days later sprayed with aqueous spray broths of active substances of the formula I. The amount of active substance corresponded to a rate of application of 5 kg of active substance per hectare. Fourteen days after application the growth of the grasses was evaluated according to the following linear rating:
  1 = strong inhibition (no growth from the time of application)
  9 = no inhibition (growth as untreated control)
The following results were obtained

| Comp. No. | a | b | c | d | Comp. No. | a | b | c | d |
|---|---|---|---|---|---|---|---|---|---|
| 2 | 1 | 1 | 1 | 1 | 14 | 3 | 2 | 3 | 4 |
| 3 | 1 | 1 | 1 | 1 | 15 | 4 | 3 | 2 | 3 |
| 4 | 1 | 1 | 1 | 2 | 16 | 2 | 3 | 1 | 3 |
| 5 | 2 | 3 | 2 | 3 | 17 | 2 | 4 | 3 | 2 |
| 6 | 2 | 2 | 2 | 4 | 18 | 3 | 4 | 3 | 3 |
| 8 | 2 | 1 | 1 | 2 | 19 | 1 | 1 | 1 | 1 |
| 9 | 4 | 2 | 2 | 3 | 20 | 1 | 1 | 1 | 2 |
| 10 | 4 | 3 | 2 | 4 | 21 | 1 | 1 | 1 | 1 |
| 11 | 3 | 3 | 4 | 4 | 22 | 2 | 1 | 2 | 2 |
| 12 | 4 | 3 | 3 | 4 | ** | 9 | 9 | 9 | 9 | a = *Lolium perenne*
b = *Poa pratensis*
c = *Festuca ovina*
d = *Dactylis glomerata*
** = Control

What I claim is:
1. A compound of the formula

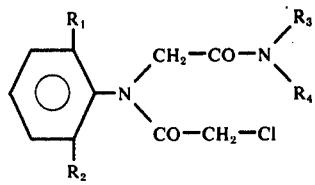

(I)

wherein $R_1$ and $R_2$ each represents methyl or ethyl, or wherein $R_1$ represents chlorine or methoxy and $R_2$ represents methyl, and $R_3$ and $R_4$ each represents hydrogen, methyl or ethyl.

2. A compound according to claim 1, wherein in the formula I $R_1$ represents chlorine or methoxy $R_2$ represents methyl, $R_3$ represents hydrogen, methyl or ethyl, and $R_4$ represents methyl or ethyl.

3. A compound according to claim 1, wherein in the formula I $R_1$ and $R_2$ each represents methyl or ethyl, $R_3$ represents hydrogen, methyl or ethyl, and $R_4$ represents methyl or ethyl.

4. A compound according to claim 1, wherein in the formula I $R_1$ and $R_2$ each represents methyl or ethyl, or wherein $R_1$ represents chlorine and $R_2$ represents methyl, $R_3$ and $R_4$ each represents hydrogen, methyl or ethyl, the total number of carbon atoms in $R_1$ to $R_4$ not exceeding six.

5. N-methyl-[N'-(2,6-dimethylphenyl)-N'-chloroacetyl-amino]-acetamide, according to claim 1.

6. N-Methyl-[N'-(2-methyl-6-ethylphenyl-N'-chloroacetyl-amino]-acetamide, according to claim 1.

7. N,N-dimethyl-[N'-(2,6-dimethylphenyl)-N'-chloroacetylamino]-acetamide, according to claim 1.

8. N,N-dimethyl-[N'-(2-methyl-6-ethylphenyl)-N'-chloroacetylamino]-acetamide, according to claim 1.

9. N-ethyl-[N'-(2,6-dimethylphenyl)-N'-chloroacetyl-amino]-acetamide, according to claim 1.

10. N-ethyl-[N'-(2-methyl-6-ethylphenyl)-N'-chloroacetyl-amino]-acetamide, according to claim 1.

11. N,N-dimethyl-[N'-(2-chloro-6-methylphenyl)-N'-chloroacetyl-amino]-acetamide, according to claim 1.

12. N-methyl-N-ethyl-[N'-(2,6-dimethylphenyl)-N'-chloroacetyl-amino]-acetamide, according to claim 1.

13. N-methyl-[N'-(2,6-diethylphenyl)-N'-chloroacetyl-amino]-acetamide, according to claim 1.

14. [N-(2,6-dimethylphenyl)-N-chloroacetyl-amino]-acetamide, according to claim 1.

15. N-methyl-N-ethyl-[N'-(2-methyl-6-ethylphenyl)-N'-chloroacetyl-amino]-acetamide, according to claim 1.

16. A plant growth retarding composition which comprises an effective amount of a compound of the formula I according to claim 1 together with a suitable inert carrier therefor.

17. A method for retarding the growth of grasses and crop plants which comprises applying thereto an effective nonlethal amount of a compound according to claim 1.

18. The method of claim 17, wherein said compound is N-methyl-[N'-(2-methyl-6-ethylphenyl-N'-chloroacetylamino]-acetamide.

19. The method of claim 17, wherein said compound is N-ethyl-[N'-(2,6-dimethylphenyl)-N'-chloroacetylamino]-acetamide.

20. The method of claim 17, wherein said compound is N,N-dimethyl-[N'-(2,6-dimethylphenyl-N'-chloroacetylamino]-acetamide.

* * * * *